United States Patent

Gadd

[11] Patent Number: 5,447,511
[45] Date of Patent: Sep. 5, 1995

[54] TICK REMOVAL TOOL

[75] Inventor: Richard J. Gadd, Stony Point, N.Y.

[73] Assignee: SCS Ltd., Stony Point, N.Y.

[21] Appl. No.: 364,434

[22] Filed: Dec. 27, 1994

Related U.S. Application Data

[63] Continuation of Ser. No. 132,459, Oct. 6, 1993, abandoned.

[51] Int. Cl.[6] .............................................. A61B 19/00
[52] U.S. Cl. ...................................................... 606/131
[58] Field of Search ....................... 606/1, 131, 205–211

[56] References Cited

U.S. PATENT DOCUMENTS

| | | | |
|---|---|---|---|
| 344,150 | 6/1886 | Wigmore . | |
| 671,337 | 4/1901 | Gibson . | |
| 1,991,816 | 2/1935 | Moseley . | |
| 2,569,237 | 9/1951 | Hall . | |
| 4,213,460 | 7/1980 | Weiner | 606/131 |
| 4,269,190 | 5/1981 | Behney . | |
| 4,303,268 | 12/1981 | Davidson | 606/210 |
| 4,494,542 | 1/1985 | Lee | 606/138 |
| 4,901,723 | 2/1990 | Platek . | |
| 4,938,764 | 7/1990 | Glaberson | 606/131 |
| 4,976,718 | 12/1990 | Daniell | 606/131 |
| 5,002,323 | 3/1991 | Idsund | 606/210 |
| 5,078,729 | 7/1992 | Eichhorn | 606/210 |
| 5,116,347 | 5/1992 | Buttler | 606/131 |
| 5,246,449 | 9/1993 | Webster | 606/131 |

Primary Examiner—Stephen C. Pellegrino
Assistant Examiner—Glenn K. Dawson
Attorney, Agent, or Firm—Darby & Darby

[57] ABSTRACT

A tool for removing anchored ticks from the skin of an animal or a human. The tick removal tool includes an elongated member having a longitudinal axis, a lateral axis, a forward edge and a handle end. A tapered slot is formed within the elongated member. The tapered slot is located along the longitudinal axis and diverges towards and merges with the forward edge. The tool is manipulated so that the mouth parts and head of the tick that are embedded in the skin of the animal or human are positioned and secured within the tapered slot. The now secured tick may be easily removed by movement of the tool.

10 Claims, 1 Drawing Sheet

TICK REMOVAL TOOL

This is a continuation, of application Ser. No. 08/132,459, filed Oct. 6, 1993, now abandoned.

FIELD OF THE INVENTION

This invention generally relates to devices for removing foreign objects from the skin surface and, in particular, to devices for removing ticks from the skin of animals and humans.

BACKGROUND OF THE INVENTION

Any animal (including humans) that travels through the underbrush of the outdoors, especially grasses, is susceptible to attack by a great variety of ticks, many of which often carry diseases including the potentially fatal Lyme disease and Rocky Mountain Spotted Fever. Once entangled within the hair of an animal host (e.g., a dog) the tick will eventually work its way to the surface of the animal's skin and cement its head beneath the surface of the skin into direct fluid communication with the bloodstream of the host animal or human. If not removed from the skin of the host, the tick will feed on the blood of the host. During this feeding period, the tick is likely to transmit a disease carrying organism into the bloodstream of the host, endangering the health, and in some cases the life of the host.

In recent years, with the onset of Lyme disease (caused by a spirochete bacterium that is transmitted by tiny ixodes classification ticks, among others, tick removal from pets and humans has become evermore important. The ixodes tick that is responsible for lyme disease is present on animals, plants and vegetation throughout the spring, summer and early fall. The recent occurrence of mild winters has permitted year round activity in many locations. Many relatively simply mechanical devices for removing ticks from the surface of the skin have been developed and are commercially available. These devices are not only fairly complex and relatively expensive, many fail to effectively remove a wide variety of the tick species typically encountered by animals and humans, such as the smaller ixodes tick responsible for lyme disease.

Many of the existing devices operate with a tweezer-like pinching action and are designed to engage and remove larger ticks which have already become engorged with the hosts blood. Using a device that relies upon a tweezer-like action to remove a tick may be unnecessarily painful to a host because the relatively bulky pivoting members of such devices typically pinch and remove nearby hair from the pet or person. Also, devices that require a pinching action for operation may squeeze the body of the tick sufficiently to rupture it. In such instance, the release of bacteria from the tick may be forced into the bloodstream of the host prior to the removal of the tick. Another risk of using these devices includes the incomplete removal of the entire tick. Because the penetrating mouth parts of the tick are generally embedded and cemented in the skin of the host that has been attacked, the body of the tick has a tendency to separate, when it is pulled or pried away from the skin surface, leaving the tick's mouth parts embedded in the skin of the host where they can continue to be a source of irritation, and secondary infection. Accordingly, in removing a tick from the skin surface, it is particularly important because of possible bacterial infection, to remove the entire body of the tick without rupturing or otherwise damaging it.

U.S. Pat. No. 4,938,764 issued to Glabeson discloses a tick remover which includes a handle assembly supporting a wire loop assembly. The wire loop defines an elongated channel into which the "neck" of a feeding tick may be positioned. The tick, once engaged within the channel of the wire loop may be pried from the surface of the animal's skin. Although the problem of accidentally entangling nearby hair is eliminated with the patented arrangement, this device is ineffective at removing smaller ticks because the elongated channel of Glabeson's device is simply rounded, not tapered. Furthermore, the closed loop in the Glabeson device makes it difficult to position the tick within the channel. An awkward movement is required to position a feeding tick within the Glabeson device, at times causing the tick to become obstructed from view. This may result in incomplete removal of the tick.

OBJECTS OF THE INVENTION

It is therefore an object of the invention to provide a device for removing ticks from the surface of human or animal skin which overcomes the problems of the prior art.

It is another object of the invention to provide such a tick removal device which is easily positionable about a tick.

It is another object of the invention to provide such a tick removal device which removes ticks from a skin surface without squeezing them and therefore without rupturing them prior to their removal.

It is another object of the invention to provide such a tick removal device which avoids accidental entanglement with the hair of the animal.

It is another object of the invention to provide such a tick removal device which may be used to effectively remove ticks of many different sizes.

It is yet another object of the invention to provide such a tick removal device which is inexpensive to manufacture, simple in construction and highly durable.

Yet another object of the invention is to provide a tick removal device that is easily used by the average untrained person to capture and remove a tick.

Another object of the invention is to provide a tick removal device that is portable and can be carried on one's person without any need for special cases or boxes to protect the device from damage.

SUMMARY OF THE INVENTION

The present invention comprises a simple tool for removing anchored ticks from the skin of an animal or human host.

The tick removal tool of the present invention comprises an elongated member having a longitudinal axis, a lateral axis, a forward edge and a handle end. A tapered slot is formed within the forward edge of the elongated member. The tapered slot is located along the longitudinal axis and diverges towards and merges with the forward edge. The elongated member has a generally flat cross section at the handle end and tapers to a generally convex cross section at the forward edge of the tapered slot. In use, the tool is manipulated so that the penetrating mouth parts of the tick are positioned and secured within and at the narrowest portion of the tapered slot while the body of the tick rests upon the top portion of the convex section. The now secured tick may be easily removed by lifting the forward end of the tool upwards, thereby lifting the entire tick body off the skin surface.

DETAILED DESCRIPTION OF THE PREFERRED EMBODIMENT

Figure 1:
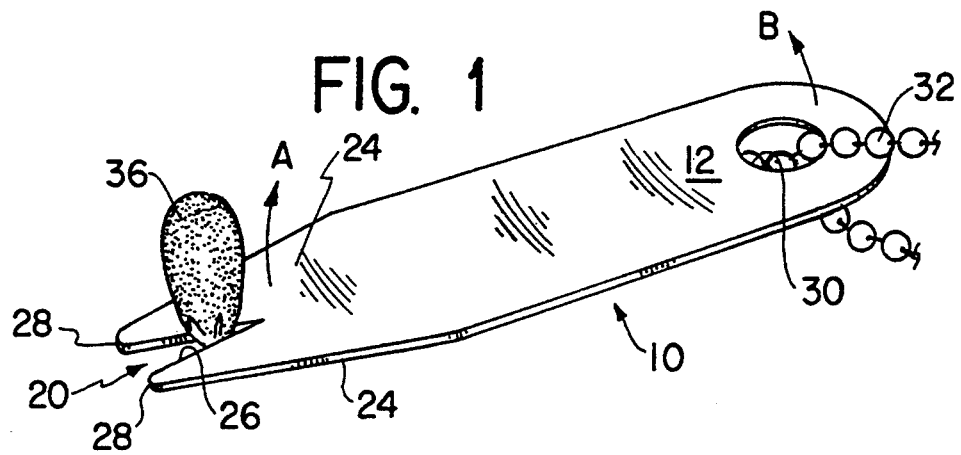
FIG. 1 is a perspective view of the present tick removing tool positioned about a tick anchored within a portion of skin.
Figure 2:
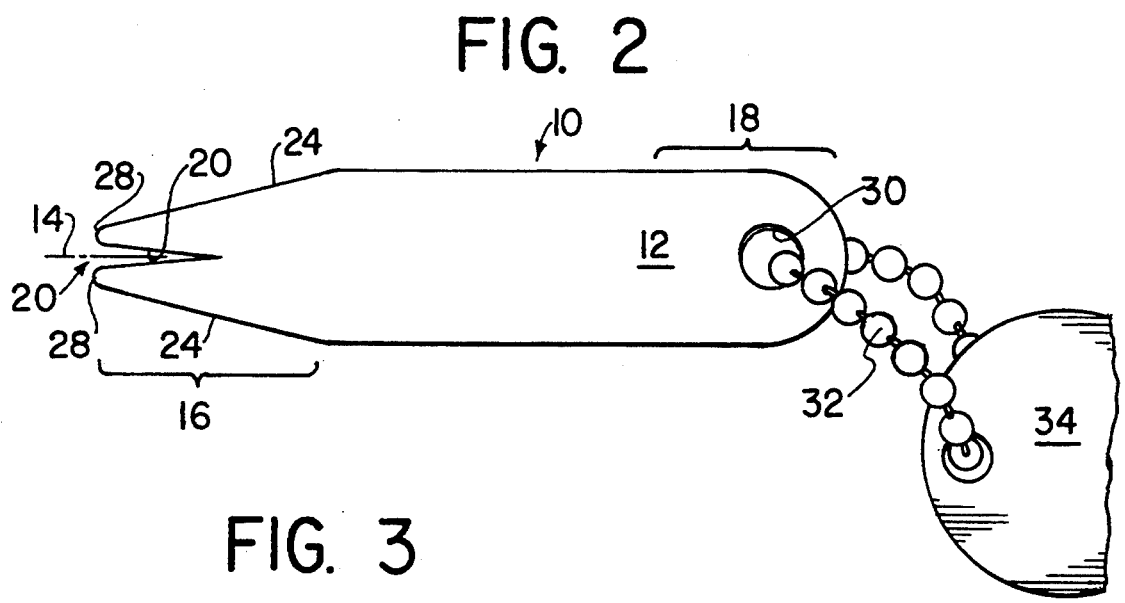
FIG. 2 is a plan view of the tick removing tool in accordance with the invention showing a tapered engagement slot.
Figure 4:
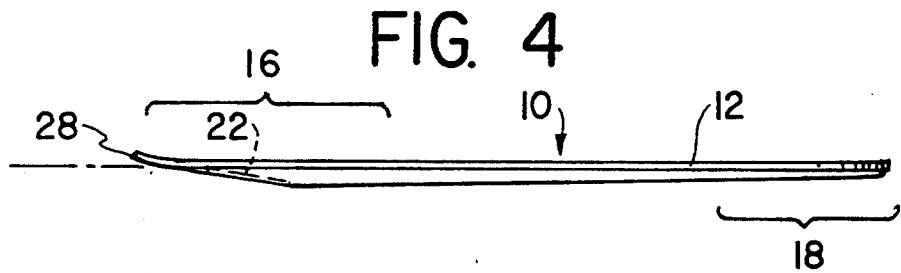
FIG. 4 is a longitudinal cross-sectional view of the tick removing tool in accordance with the invention, taken along lines 4—4 of FIG. 2.

Referring to FIGS. 1, 2 and 4 the tick removing tool 10 of the present invention comprises an elongated blade member 12 having a central longitudinal axis 14, a forward engagement section 16 and a rearward handle section 18 (which is preferably rounded). An upper surface of the blade member is preferably smooth. A tapered (generally V-shaped) engagement slot 20 is provided along the longitudinal axis 14 adjacent the forward engagement end 14. The central engagement slot 20 defines two arms 22 formed integral with the elongated blade 12. Each arm 22 includes an outer edge 24, a slot edge 26 and a front end 28. The slot edge 26 and the outer edge 24 of each arm 22 are preferably tapered towards each respective front end 28. The front end 28 of each tapered arm 22 is preferably rounded.

Figure 3:
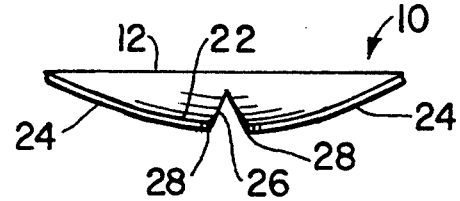
FIG. 3 is a sectional view of the tick removing tool shown in FIG. 2 taken along the lines, 3—3.

The entire length of the elongated blade 12, or a portion of the forward engagement section 16 thereof is preferably curved laterally with respect to the longitudinal axis 14 (i.e., across the width of the tool 10). An example of such a curvature is shown in FIGS. 3 and 4, which are sectional views taken along the corresponding lines 3—3 and 4—4 or FIG. 2, respectively. As shown in FIGS. 3 and 4, the preferred sectional profile of the elongated blade 12, in this example, is flat (i.e., no curve) at the handle section 18 and, starting near the forward engagement section 16, the blade member 12 assumes a concave curvature. The degree of curvature increases gradually advancing towards the forward engagement section 16. In an alternative arrangement, the forward section 16 may be curved evenly throughout (i.e., with a uniform radius curve), not shown.

The elongated blade 12 is preferably made from a strong thin resilient material such as spring steel stock or certain plastics capable of being machined by stamping and cutting such as styrene and polypropylene or polyvinylchloride (PVC) or injected into a mold using a polycarbonate, or acrylic thermoplastic resin. In one preferred embodiment, the preferred material; spring (stainless) steel stock, has a thickness of about 0.012 inches. However, the device can also be made of softer malleable metals such as aluminum, copper and magnesium. The elongated blade 12 may be cut and bent to shape using any appropriate process steps, such as cutting and stamping. One preferred tick removing tool 10 in accordance with the invention has an elongated blade which is about 2.25 inches in length and about 0.5 inches wide. The slot of this preferred tick removing tool is about 0.3 inches long and includes a widest slot width of about 0.042 inches, tapering down to a slot width of about 0.005 inches.

The material and thickness chosen for the tick removing tool 10 preferably permits controlled bending and flexing throughout the handle section 18, as desired by the user. Forming the handle section 18 with a cross section, having an overall longitudinal curve with a relatively large radius of curvature has been found to be useful to facilitate the operation of the tick removing tool 10. This overall longitudinal curve may either be provided (e.g. by stamping on a clawed form) during the manufacture of the elongated blade 12, or formed by the user later on by simply bending the handle by hand to a curved shape.

As described above, the forward engagement section 16 of the tool has a uniform curvature i.e. single radius for the entire forward section, or as in the example described above, a curvature of progressively smaller radius, advancing forward. The purpose of the curvature of the forward engagement section 16 is to increase the overall structural integrity of the elongated blade 12 and to aid the user in positioning the tapered slot 20 around the mouth parts and head and under the body of a tick, as described in greater detail below.

The rounded front ends 28 of each arm 22 facilitate smooth insertion of the tick into the tapered slot 20. The entire tick removal tool 10, or at least the forward engagement section 16 is preferably highly polished (if made from a metal, such as spring steel) or made smooth if non metallic, to further facilitate the non-abrasive, non-traumatic positioning of a tick within the rearmost portion of the tapered slot 20. The rounded arm ends and the smooth surfaces ensure that discomfort to the host will be minimized and, perhaps more importantly, that the tick itself will not be damaged, in particular, decapitated, or squeezed during the process of inserting positioning the tick removing tool 10. The smooth surfaces and the rounded edges of the tick removing tool 10 also discourage hair entanglement while positioning the tool about the tick.

An aperture 30 may be provided at any appropriate location on the elongated blade 16 for receiving a cord or chain 32, so that the tick removing tool 10 may be secured to another element such as a key-ring (not shown) or an information tag 34. The tick removal tool of the present invention may also be attached or made an integral part of another device or tool such as a folding knife, nail clipper or utility tool for convenience, while still retaining the tick removal function.

In operation, referring to FIG. 1, the user first locates a feeding tick 36 anchored within the skin 38 of an animal or human. Any hair/fur is pushed aside to clearly expose the underlying tick 36. The tick removing tool 10 is held by the handle section 18 and carefully positioned between the body of the tick 36 and the surface of the skin 38 (i.e. the mouth parts and head of the tick 36) so that the mouth parts and head of the tick 36 slides easily within the slot 20. The tick removing tool 10 is used with the curved forward engagement section facing upward away from the skin 38 (concave surface facing away from the skin 38).

Once the mouth parts and head of the tick 36 are positioned within the slot 20, the entire tool 10 is slid towards the tick 36 until the tick's mouth part becomes securely pinched between the arms 22 and at the rear of the tapered slot 20. Being laterally curved, the two arms 22 on either side of the engagement slot 20 tend to flex apart as the tick is pinched into the slot 20. This flexing action of the arms 22 discourages the severing of the tick's head from its body, should the tick removing tool 10 be excessively advanced.

When the tick is securely pinched between the arms 22 of the tick removing tool 10, the forward engagement section 16 of the tool 10 is simply lifted upwards and away from the surface of the skin 38 (following a direction represented by arrow "A" in FIG. 4) to dislodge the tick 36. Also, depending on the size of the tick 36, the tick removing tool 10 may be carefully pivoted against the skin 38 (following a motion represented by arrow "B" in FIG. 4) using the anchored tick 36 as a fulcrum to literally pry the tick upwards and away from the skin 38. In the preferred embodiment (made of resilient metal) the blade 12 has a spring bias action that acts downwardly (toward the skin surface of the host) when in use. This also helps to facilitate manipulation of the device and safe removal of the entire tick body.

Once removed from the skin 38, the tick 36 may be drawn from the tapered slot 20 with a tissue and appropriately destroyed. The device can then be cleansed and sterilized for reuse.

What is claimed is:

1. A tool for removing ticks from the skin of a host, said tool comprising:

a single-piece member having a forward end, a handle end, and a longitudinal axis, said handle end located opposite said forward end, said single-piece member having a constant thickness between said handle end and said forward end, said member having an upper surface and a lower surface and being curved upwardly about its longitudinal axis, said member including two equal length arms, each of said arms having a straight slot edge on one side and terminating in a rounded front end, said slot edges being opposed to one another and defining between them a fixed V-shaped tapered slot having a predetermined and consistent taper which converges at a convergent point, said V-shaped slot located adjacent to and formed integral with said forward end of said member, said V-shaped slot having a wide mouth at said forward end of said member, said V-shaped tapered slot being shaped to receive a portion of a tick that is attached to the skin of a host and secure said tick sufficiently to allow said tick to be pulled from said skin with said tool.

2. The tick removing tool according to claim 1, wherein said member comprises stainless steel.

3. The tool according to claim 1, wherein said member comprises spring steel.

4. The tool according to claim 1, wherein said member comprises a resilient plastic material.

5. The tool according to claim 4, wherein said member comprises a resilient polycarbonate plastic.

6. The tool according to claim 4, wherein said member comprises polyvinylchloride.

7. The tool according to claim 4, wherein said member comprises a resilient acrylic plastic.

8. The tick removing tool according to claim 1, wherein said V-shaped slot converges into said member and towards said handle end along the longitudinal axis and wherein said wide mouth has a width which lies within a range between about 0.030 and 0.050 inches.

9. The tool according to claim 8, wherein said member is made from spring steel.

10. The tool according to claim 8, wherein said member comprises a malleable metal.

* * * * *